United States Patent [19]

Moore

[11] Patent Number: 4,551,542

[45] Date of Patent: Nov. 5, 1985

[54] REGENERATION OF 6-FLUORO-4-CHROMANONE FROM 6-FLUORO-4-UREIDOCHROMAN-4-CARBOXYLIC ACID

[75] Inventor: Bernard S. Moore, Waterford, Conn.

[73] Assignee: Pfizer Inc., New York, N.Y.

[21] Appl. No.: 655,006

[22] Filed: Sep. 26, 1984

[51] Int. Cl.$^4$ .......................................... C07D 311/68
[52] U.S. Cl. ..................................................... 549/401
[58] Field of Search .............................. 549/401, 404

[56] References Cited

U.S. PATENT DOCUMENTS

| | | | |
|---|---|---|---|
| 4,117,230 | 9/1978 | Sarges | 548/309 |
| 4,130,714 | 12/1978 | Sarges | 548/309 |
| 4,286,098 | 8/1981 | Sarges | 548/309 |
| 4,348,526 | 9/1982 | Sarges | 548/309 |
| 4,431,828 | 2/1984 | Cue et al. | 549/401 |
| 4,435,578 | 3/1984 | Cue et al. | 548/309 |

OTHER PUBLICATIONS

Sarges et al., J. Org. Chem., 47, 4081 (1982).

*Primary Examiner*—Nicky Chan
*Attorney, Agent, or Firm*—Charles J. Knuth; Albert E. Frost; J. Trevor Lumb

[57] ABSTRACT

6-Fluoro-4-chromanone can be regenerated from (R)-6-fluoro-4-ureidochroman-4-carboxylic acid, or from mixtures of (R)-6-fluoro-4-ureidochroman-4-carboxylic acid and its racemic modification, by oxidation with a permanganate, especially potassium permanganate. 6-Fluoro-4-chromanone is a chemical intermediate useful for preparing sorbinil, an aldose reductase inhibitor which can be used in clinical medicine for the control of the chronic complications of diabetes. (R)-6-Fluoro-4-ureidochroman-4-carboxylic acid and its racemic modification are by-products from the production of sorbinil from 6-fluoro-4-chromanone.

11 Claims, No Drawings

REGENERATION OF 6-FLUORO-4-CHROMANONE FROM 6-FLUORO-4-UREIDOCHROMAN-4-CARBOXYLIC ACID

BACKGROUND OF THE INVENTION

Diabetes mellitus is a metabolic disorder which afflicts a significant percentage of the human population. It is characterized by reduced carbohydrate utilization, leading to hyperglycemia, with resulting glycosuria and polyurea, giving symptoms of thirst, hunger, emaciation and finally diabetic coma. Although the short-term adverse effects of diabetes (e.g. diabetic coma) can usually be controlled by the administration of an oral hypoglycemic agent or insulin, in many cases of diabetes long-term complications develop, especially neuropathy and ocular problems such as retinopathy and cataract formation.

One approach to the control of the long-term adverse effects of diabetes is treatment with an inhibitor of the aldose reductase enzyme, with a view to blocking the reduction of glucose to sorbitol. One such aldose reductase inhibitor which is of use in controlling the chronic complications of diabetes is sorbinil, the chemical compound having the following structural formula:

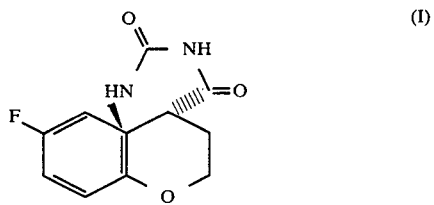
(I)

Thus, sorbinil is one of the optical antipodes of 6-fluoro-spiro[chroman-4,4'-imidazoline]-2',5'-dione. Specifically, it is the dextrorotatory isomer of 6-fluoro-spiro[chroman-4,4'-imidazolidine]-2',5'-dione, and it has the (S)-configuration at its asymmetric center based on the Cahn-Ingold-Prelog system of designating absolute configurations. (Sarges, U.S. Pat. No. 4,130,714).

A key raw material for the preparation of sorbinil is the bicyclic ketone, 6-fluoro-4-chromanone (II). In one method of producing sorbinil, 6-fluoro-4-chromanone is converted in several steps into racemic (RS)-6-fluoro-4-ureidochroman-4-carboxylic acid (III), from which the desired isomer, (S)-6-fluoro-4-ureidochroman-4-carboxylic acid (IV), is obtained by resolution with an optically active amine, and cyclized to sorbinil using glacial acetic acid. Cue and Moore, U.S. Pat. No. 4,435,578—see SCHEME I.

However, resolution of the racemic ureido-acid (III) produces, as a by-product, (R)-6-fluoro-4-ureidochroman-4-carboxylic acid (V), i.e. the isomer with the wrong stereochemistry at C-4 for cyclization to sorbinil. The (R)-ureido-acid (V) can be recovered from the resolution step, and in practice it is usually contaminated with varying amounts of the (RS)-ureido-acid (III).

Accordingly, it is an object of the present invention to provide a process for converting the (R)-ureido-acid (V), and mixtures thereof with (RS)-ureido-acid (III), back into 6-fluoro-4-chromanone by oxidation with a metal permanganate. The regenerated chromanone (II) can be reconverted into racemic ureido-acid (III) and thence to additional sorbinil. This recycling technique of (R)-ureido-acid (V) avoids economic losses and waste disposal problems in sorbinil synthesis, and thereby greatly increases overall synthesis efficiency.

SCHEME I

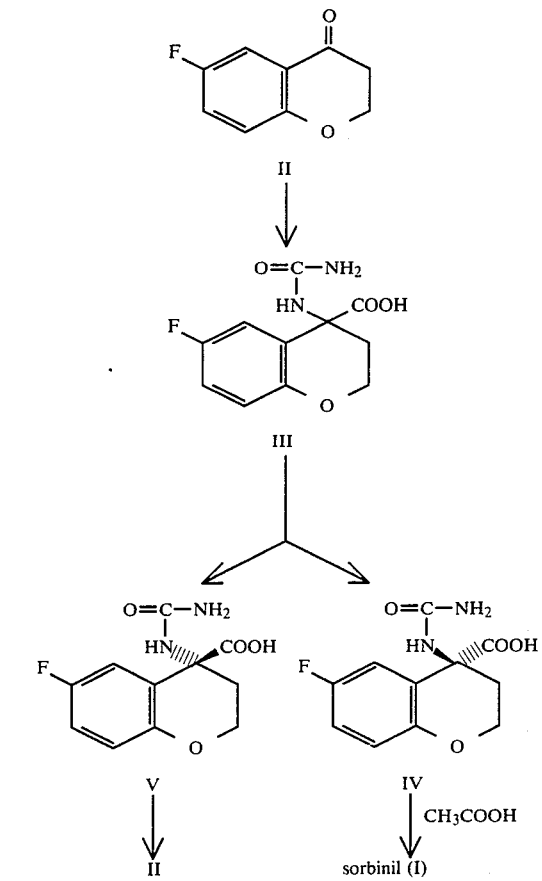

One method for regenerating 6-fluoro-4-chromanone from (R)-ureido-acid (V), or a mixture with its racemic counterpart, has been described in U.S. Pat. No. 4,431,828. However, the process of the present invention possesses advantages over the prior regeneration process. The present process involves a single oxidation step, which is easy to carry out, operates directly on the ureido-acid, and produces the chromanone (II) in pure form. The prior art process requires a hydrolysis step prior to oxidation, and the chromanone (II) produced contains a 4-chloroimino contaminant, which has to be removed by hydrogenation.

SUMMARY OF THE INVENTION

This invention provides a process for the regeneration of 6-fluoro-4-chromanone (II) from (R)-6-fluoro-4-ureidochroman-4-carboxylic acid (V) or a mixture of (R)- and (RS)-6-fluoro-4-ureidochroman-4-carboxylic acid (V and III), which comprises:

reacting said (R)-6-fluoro-4-ureidochroman-4-carboxylic acid or mixture of (R)- and (RS)-6-fluoro-4-ureidochroman-4-carboxylic acid with a metal permanganate, in an aqueous or partially aqueous solvent system, at a temperature in the range from 10° to 70° C., and at a pH in the range from 3 to 7, viz.:

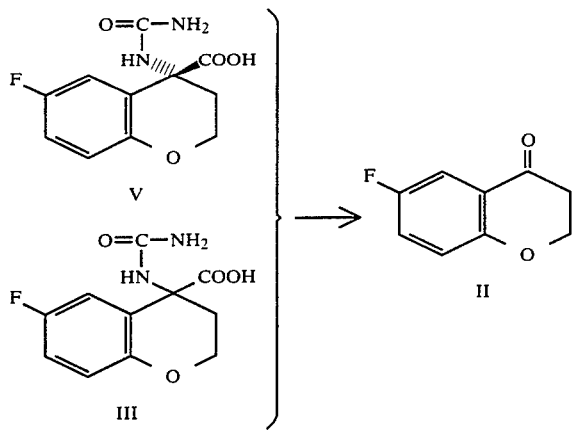

Alkali metal and alkaline earth metal permaganates can be used for the process of present invention, but the preferred reagent is potassium permanganate. The process is preferably carried out using 0.7 to 2.0 molar equivalents, especially 1.0 to 1.2 equivalents, of potassium permanganate in water-acetic acid mixtures.

DETAILED DESCRIPTION OF THE INVENTION

The present invention provide a process for the oxidation of the (R)-ureido-acid (V), or a mixture of the (R)-ureido-acid (V) and its corresponding racemate (III), to 6-fluoro-4-chromanone, using a permanganate, and it can be used irrespective of the source of the ureido-acid substrate. Moreover, when a mixture of (R)- and (RS)-ureido-acids is used, the process of this invention can be used irrespective of the ratio of the (R)- and (RS)-substrates.

However, the process of this invention is particularly useful for recycling the by-product obtained after removal of (S)-ureido-acid (IV) from racemic ureido-acid (III) in a synthesis of sorbinil (U.S. Pat. No. 4.435,578). Thus, in a typical sorbinil synthesis, the (RS)-ureido-acid (III) is contacted with about one molar equivalent of an optically-active amine in a suitable solvent, under conditions such that the diastereomeric salt containing the (S)-ureido-acid (IV) precipitates from the reaction medium and it can be removed by filtration. Typical optically-active amines which are used are D-(+)-(1-phenylethyl)amine and L-(—)-ephedrine, and a suitable solvent system is aqueous methanol. The precipitated salt containing the (S)-ureido-acid is then converted into sorbinil, usually by treatment with glacial acetic acid. The mother liquors after removal of the salt containing the (S)-ureido-acid (IV) by filtration are then usually freed from the methanol, basified to a pH of about 10 or 11 and extracted with a volatile, water-immiscible, organic solvent to remove the resolving amine. Acidification of the resulting aqueous solution causes precipitation of a mixture of (R)- and (RS)-6-fluoro-4-ureidochroman-4-carboxylic acid which is suitable for recycling to 6-fluoro-4-chromanone by the process of this invention. In such a mixture, the ratio of said (R)-ureido-acid (V) to said (RS)-ureido-acid (III) is usually in the range from 20:1 to 1:2, especially about 2:1.

The process of this invention involves a single step; namely, oxidation with permanganate. The process is normally carried out simply by contacting the ureido-acid substrate with the permanganate in an appropriate solvent system, until conversion into the chromanone (II) is complete. An alkali metal permanganate, e.g. lithium, sodium or potassium permanganate, or an alkaline earth metal permanganate, e.g. calcium or magnesium permanganate, can be used. However, the preferred reagent is potassium permanganate.

An appropriate solvent system is one which will dissolve the ureido-acid substrate to a significant degree, does not have any adverse effect on the starting ureido-acid substrate or the chromanone product, is not oxidized by permanganate to a significant extent, and permits easy isolation of the chromanone product. In practice, water is a convenient solvent which is commonly used. If desired certain organic co-solvents, such as tetrahydrofuran, dioxane, or low-molecular weight ethers of ethylene glycol or diethyleneglycol (e.g. 1,2-dimethoxyethane) can be added. However, it is usually preferable that the reaction medium remains homogeneous. Moreover, it is usually advantageous to conduct the process of this invention at a neutral or acidic pH. In particular a pH in the range form 3.0 to 7.0 is preferred, and this is achieved by the addition of an acidifying agent. A wide variety of acidifying agents can be added, the major requirement of such an agent being that it does not affect the ureido-acid substrate or chromanone product, and it is unaffected by the permanganate oxidant. Both inorganic and organic acidifying agents can be added, and typical agents are hydrochloric acid, sulfuric acid, nitric acid, phosphoric acid, acetic acid, methanesulfonic acid and toluenesulfonic acids. A particularly convenient acidifying agent is glacial acetic acid. Indeed, water containing a small volume of acetic acid represents a preferred solvent system for the process of this invention, especially water containing from 0.5 to 3 percent by volume of acetic acid.

The order of addition of the ureido-acid substrate and the permanganate oxidant to the solvent is not critical, and the two reactants can be added in either order. Also, it is sometimes convenient to treat a solution of the ureido-acid substrate with the permanganate portionwise, either as a solid or as an aqueous solution, as the oxidation proceeds. In that way, permanganate can be added in small amounts until a slight excess persists, i.e. the starting ureido-acid substrate is effectively titrated with the permanganate. This technique is particularly convenient when the ureido-acid substrate contains minor impurities which are also subject to permanganate oxidation. The process of the present invention is carried out at a pH in the range from 3.0 to 7.0. Although this is normally achieved by adding the starting ureido-acid substrate in its free carboxylic acid form, the ureido-acid substrate can by introduced into the reaction medium in the form of a carboxylate salt. The amount of added acidifying agent is then adjusted accordingly, to achieve the required pH for the oxidation. It is, of course, the pH at which the oxidation is run that determines the precise nature of the ureido-acid substrate (free acid or carboxylate salt) which undergoes oxidation. The ureido-acid substrate can be introduced into the reaction medium as a variety of salts. However, it is preferable that the cationic counterion is not susceptible to permanganate oxidation. Thus, favorable salts of the ureido-acid substrate which can be used are alkali metal salts (e.g. lithium, sodium or potassium salts) or alkaline earth metal salts (e.g. calcium or magnesium salts). On the other hand, amine salts, while still operable, are not generally favored.

The oxidation reaction of this invention can be carried out over a wide range of temperature. However, to ensure a convenient rate of reaction and achieve convenient reaction times, reaction temperatures from 10° to 70° C., and preferably 20° to 50° C., are commonly used. At a reaction temperature of 20° to 50° C., reaction times of a few hours, e.g. 2 to 10 hours are quite common.

An advantageous feature of the process of this invention resides in the ease of isolation of the product. At the completion of the oxidation, any excess permanganate and the manganese dioxide by-product can be reduced and solubilized by the addition of bisulfite, e.g. solid sodium meta-bisulfite, and then the 6-fluoro-4-chromanone can be recovered by standard techniques, e.g. filtration or extraction into a water-immiscible, volatile, organic solvent. Evaporation of the organic solvent then affords the desired chromanone II. The chromanone thus obtained directly from the process of this invention is usually of sufficient quality for use in further sorbinil synthesis, e.g. according to the methods of U.S. Pat. Nos. 4,130,714 or 4,435,578; however, the chromanone product can be purified by standard procedure, such as chromatography or recrystallization e.g. from methanol, if desired.

Thus, the 6-fluoro-4-chromanone recovered from the process of this invention can be used according to U.S. Pat. No. 4,435,578, as follows:

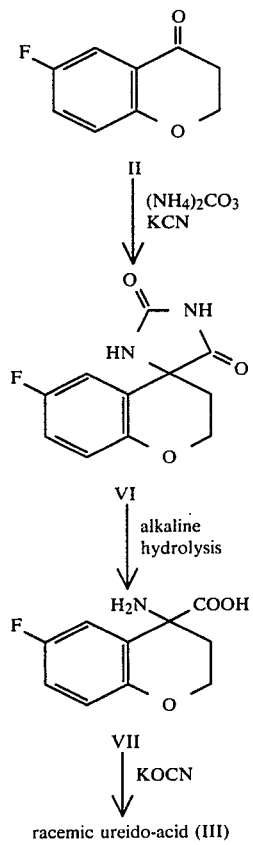

The 6-fluoro-4-chromanone is reacted with an alkali metal cyanide (e.g. potassium cyanide) and ammonium carbonate in a polar solvent, such as aqueous ethanol, at about 65° C., for several hours, to give the racemic hydantoin (VI). The hydantoin (VI) is hydrolyzed to the racemic amino-acid (VII) under basic conditions, e.g. using about four molar equivalents of sodium hydroxide, or two molar equivalents of barium hydroxide octahydrate, in water, under reflux, for several hours. The amino-acid (VII) is then treated with two molar equivalents of potassium cyanate in water, at room temperature. The reaction proceeds quite rapidly to give the racemic ureido-acid (III) which is resolved by salt formation with an optically-active amine, as described previously. The amine salt of the (S)-ureido-acid (IV) can be converted into sorbinil by treatment with a large excess of glacial acetic acid at about 90° C. for a few hours, e.g. about two hours.

As indicated hereinbefore, sorbinil is an aldose reductase inhibitor, and it is useful for administration to diabetic human subjects for the control of chronic complications of diabetes, such as neuropathy, retinopathy and cataract formation. For such purposes, sorbinil is normally compounded into pharmaceutical compositions, e.g. tablets, capsules, aqueous suspensions or injectable solutions, according to standard pharmaceutical practice, and administered either orally or parenterally. Sorbinil is normally administered to a human patient at a dosage from about 0.05 mg to about 5.0 mg per kilogram of body weight per day, in single or multiple doses. See further U.S. Pat. No. 4,130,714.

The following examples and preparations are provided solely for the purpose of further illustration.

EXAMPLE 1

6-Fluoro-4-chromanone

A mixture of 17.3 g (0.11 mole) of potassium permanganate, 7.2 g (0.12 mole) of glacial acetic acid and 1 liter of water was stirred under an atmosphere of nitrogen at room temperature until a solution was obtained (10 minutes). To the resulting solution was then added, portionwise, with stirring, during about 2 minutes, 25.4 g (0.1 mole) of a mixture of (R)- and (RS)-6-fluoro-4-ureidochroman-4-carboxylic acid (approximate composition: 70 parts (R); 30 parts (RS)). The resulting slurry was stirred for 10 minutes at 22° C., and then it was warmed slowly to 40° C. and the heat source was removed. Stirring was continued for 30 minutes, during which time the reaction temperature rose slowly to 47° C. and then it began to fall. The heat source was reapplied, and the reaction mixture was heated and stirred at 50° C. for 30 minutes.

The reaction mixture was cooled to 23° C., and 41.6 g (0.4 mole) of sodium bisulfite was added in portions during a 30 minute period, with stirring. Stirring was continued for 30 minutes at 22° C., and then the solid was recovered by filtration, washed with water and dried. This gave 30.3 g of a solid, mp 111°-113° C. The latter solid was suspended in 100 ml of water, and 15 ml of 12N hydrochloric acid was added which gave a stable pH of 1.5. The acidified mixture was extracted with dichloromethane, and the combined extracts were washed with water, dried (MgSO₄) and concentrated in vacuo to ca 30 ml of a slurry. The slurry was diluted with 100 ml of hexane and the volume was reduced to ca 50 ml by evaporation. The resulting slurry was filtered, and the solid obtained was washed with hexane and dried. This afforded 11.0 g (66% yield) of 6-fluoro-4-chromanone, mp 112°-114° C.

The nuclear magnetic resonance spectrum (60 MHz) of the product (in CDCl₃) showed absorptions at 7.9–7.0 (multiplet, 3H), 4.65 (triplet, 2H) and 2.8 (triplet 2H) ppm, downfield from internal tetramethylsilane.

EXAMPLE 2

6-Fluoro-4-chromanone

The title compound can be prepared by oxidation of (R)-6-fluoro-4-ureidochroman-4-carboxylic acid with potassium permanganate, using the procedure of Example 1.

EXAMPLE 3

6-Fluoro-4-chromanone

When the procedure of Example 1 is repeated, but the potassium permanganate used therein is replaced by an equimolar amount of lithium permanganate, sodium permanganate, calcium permanganate or magnesium permanganate, the title product is obtained.

EXAMPLE 4

6-Fluoro-4-chromanone

A solution 29.47 kg of potassium permanganate in 246 liters of water, preheated to 50° C., was added, with stirring, to 43.27 kg of a mixture of (R)- and (RS)-6-fluoro-4-ureidochroman-4-carboxylic acid (approximate composition: 70 parts (R); 30 parts (RS)) in 946 liters of water, also preheated to 50° C. The addition took 1.5 hours and after about half of the permanganate solution had been added, glacial acetic acid was added as necessary to maintain the pH in the range 4.5 to 5.0. Stirring was continued at 50° C. and a pH of 4.5 to 5.0 for an additional 30 minutes, and then the pH was lowered to 1.5 by the addition of 31.7 liters of concentrated hydrochloric acid. To the resulting mixture was added with stirring 23.85 kg of solid sodium bisulfite, portionwise, at 50° C., while maintaining the pH at 1.5 by the addition of concentrated hydrochloric acid (ca 51.5 liters). Stirring was continued at 50° C. for 30 minutes and then the mixture was filtered. The residue was washed with water at 50° C. and dried at 50° C., giving a first crop of the title product. The mother liquors were stirred at 15°–20° C. for 3 days and then filtered. This afforded a second crop of the title product. The total yield was 25.2 kg (87% yield).

PREPARATION 1

(RS)-4-Amino-6-fluorochroman-4-carboxylic Acid

A stirred slurry of 78 g (0.33 mole) of (RS)-6-fluoro-spiro-[chroman-4,4'-imidazolidine]-2',5'-dione and 208.3 g (0.66 mole) of barium hydroxide octahydrate in 585 ml of water was slowly heated to reflux over 3 hours and refluxed 16 hours. The slurry was cooled to 80° C. and powdered NH$_4$CO$_3$ (78 g) added portionwise over 5 minutes. Moderate foaming was noted. After stirring 1.5 hours at 80° C., the mixture was cooled to 60° C., and filtered over diatomaceous earth with 2×100 ml hot water for wash. The combined filtrate and washes were stripped to 200 ml and allowed to stand overnight. 2-Propanol (600 ml) was added and the mixture heated to 70° C. to dissolve precipitated solids. The hot solution was treated with activated carbon, filtered over diatomaceous earth and washed with hot 1:1 water:2-propanol. The combined filtrate and washes were stripped to 200 ml, and water chased with 3×300 ml fresh 2-propanol. The resulting thick slurry was diluted with 200 ml additional 2-propanol, cooled to 5° C., granulated for 0.5 hour, filtered and air dried to yield title product, 63.5 g, 91.2%, mp 252°–253° C. (dec).

PREPARATION 2

(RS)-6-Fluoro-4-ureidochroman-4-carboxylic Acid

METHOD A

To a stirred slurry of 21.1 g (0.1 mole) of (RS)-4-amino-6-fluorochroman-4-carboxylic acid in 250 ml of water was added, portionwise, 16.2 g (0.2 mole) of potassium cyanate over 2.5 minutes. The almost complete solution was stirred 22 hours at 23° C., during which the pH increased from 6.8 to 9.1 and complete solution occurred. Concentrated HCl (19.0 ml) was added over 1 hour, keeping temperature 25°–29° C. The resulting slurry was granulated 1 hour (pH 3.2–3.5), and title product recovered by filtration with 150 ml water wash, partially dried in air and then for 18 hours at 50°–55° in vacuo, 20.0 g, 79%.

METHOD B

A mixture of 47.2 g (0.2 mole) of (RS)-6-fluoro-spiro[chroman-4,4'-imidazoline]-2',5'-dione, 28 g (0.7 mole) of sodium hydroxide pellets and 600 ml of water was heated under reflux for 40 hours. The reaction mixture was cooled to 24° C., and the pH was lowered from 11.8 to 5.0 with 6N hydrochloric acid. Gassing was noted below pH 8. After stirring the slurry for 20 minutes at pH 5, 32.5 g (0.4 mole) of potassium cyanate was added during 2 minutes. The mixture was stirred for 20 hours, and a small amount of solid was removed by filtration and washed with 50 ml of water. The combined filtrate and washings were adjusted from pH 8.5 to pH 4.0 using 6N hydrochloric acid. The solid which precipitated was recovered by filtration, washed with warm water and air dried to give 39.7 g (78% yield) of the title product, mp 198°–199° C. (dec.).

PREPARATION 3

(R)(+)-(1-Phenylethyl)amine Salts of 6-Fluoro-4-ureido-chroman-4-carboxylic Acid A slurry of 10.0 g (39.4 mmole) of (RS)-6-fluoro-4-ureidochroman-4-carboxylic acid in 40 ml of methanol was stirred at 45°–50° C. During 4 minutes, 4.87 g (40.1 mmole) of (R)(+)-(1-phenylethyl)amine in 45 ml of methanol was added to the resulting thin slurry, yielding a solution. The heating bath was removed, and the mixture was cooled slowly to ambient temperature, granulated for 16 hours and filtered. This afforded 6.4 g (86.6% yield) of the (R)-(1-phenylethyl)amine salt of (S)-6-fluoro-4-ureidochroman-4-carboxylic acid, mp 206°–210° C., [alpha]$_D^{25}$ = +54.3° (c=0.3, methanol).

The mother liquors from the filtration were evaporated in vacuo to give 8.3 g of a mixture of the (R)-(1-phenylethyl)amine salts of (R)-6-fluoro-4-ureidochroman-4-carboxylic acid and (RS)-6-fluoro-4-ureidochroman-4-carboxylic acid, mp 198°–200° C., [alpha]$_D^{25}$ = −35.4° (C=0.5, methanol).

The above mixture of salts is distributed between ethyl acetate and water, with the pH first adjusted to 10. The ethyl acetate layer is separated and optically active amine recovered by evaporation. The pH of aqueous phase is then adjusted to 1–2 with hydrochloric acid and extracted with fresh ethyl acetate. The organic phase is washed with additional small portions of water, dried (MgSO$_4$) and evaporated to yield a mixture of (R)- and (RS)-6-fluoro-4-ureidochroman-4-carboxylic acid.

PREPARATION 4

(1R,2S)(−)-Ephedrine Salts of 6-Fluoro-4-ureidochroman-4-carboxylic Acid

METHOD A

A slurry of 35.6 g (0.14 mole) of 6-fluoro-4-ureidochroman-4-carboxylic acid in 1.07 liters of acetone was stirred at reflux (59° C.) for 30 minutes, and then it was cooled to 54° C. To the resulting slurry was added 24.4 g (0.148 mole) of (1R,2S)-ephedrine all in one portion. The slurry thinned and a near solution resulted. After less than two minutes at 55° C. rapid crystallization began. The slurry was refluxed for 2 hours, cooled to 40° C. and the crystalline solid was recovered by filtration to give 26.1 g of the (1R,2S)-ephedrine salt of (S)-6-fluoro-4-ureidochroman-4-carboxylic acid, mp 204 (dec), [alpha]$_D^{25}$ = +37.0 (c=1, methanol).

The mothers liquors were cooled to room temperature and the further solid was recovered by filtration to give 1.3 g of material, mp 180°–185° C. (dec), [alpha]$_D^{25}$ = 0 (C=1, methanol). The filtrate was evaporated in vacuo to give 32.9 g of a mixture of the (1R,2S)-ephedrine salts of (R)-6-fluoro-4-ureidochroman-4-carboxylic acid and (RS)-6-fluoro-4-ureidochroman-4-carboxylic acid, mp 72°–90° C., [alpha]$_D^{25}$ = −55.7° (C=1, methanol).

The latter mixture of salts is partitioned between dichloromethane (150 ml) and water (150 ml) and the pH is adjusted to 11.5. The organic layer is removed and evaporated in vacuo to give recovered (1R,2S)-ephedrine. The pH of the aqueous layer is lowered to 3 to 4 and the solid which precipitates is recovered by filtration to give a mixture of (R)-6-fluoro-4-ureidochroman-4-carboxylic acid and (RS)-6-fluoro-4-ureidochroman-4-carboxylic acid.

A slurry of 25 g of the (1R,2S)-ephedrine salt of (S)-6-fluoro-4-ureidochroman-4-carboxylic acid from above in 250 ml of acetone was stirred and heated under reflux and then the mixture was cooled to 40° C. The solid was recovered by filtration to give 24 g of purified (1R,2S)-ephedrine salt of (S)-6-fluoro-4-ureidochroman-4-carboxylic acid, mp 205° C., [alpha]$_D^{25}$ = +38.2° (c=1, methanol).

METHOD B

A mixture of 100 g of (RS)-6-fluoro-4-ureidochroman-4-carboxylic acid and 374 ml of methanol was heated under reflux (65° C.) for 30 minutes and then it was cooled to 59° C. To the cooled mixture was added 7.42 ml of water followed by 68 g of (1R,2S)-ephedrine. This resulted in the formation of a heavy precipitate. The resulting mixture was refluxed for 45 minutes and then cooled to 27° C. The solid was recovered by filtration to give 70.4 g of the (1R,2S)-ephedrine salt of (S)-6-fluoro-4-ureidochroman-4-carboxylic acid, [alpha]$_D^{25}$ = +44.36° (c=1.04, methanol).

The filtrate was evaporated in vacuo to give 116.3 g of a mixture of the (1R,2S)-ephedrine salts of (R)-6-fluoro-4-ureidochroman-4-carboxylic acid and (RS)-6-fluoro-4-ureidochroman-4-carboxylic acid. This mixture of salts can be converted into a mixture of (R)-6-fluoro-4-ureidochroman-4-carboxylic acid and (RS)-6-fluoro-4-ureidochroman-4-carboxylic acid using the method described at the end of Method A, above.

PREPARATION 5

(S)(+)-6-Fluoro-spiro-[chroman-4,4′-imidazolidine]-2′,5′-dione(Sorbinil)

A mixture of 9.6 g of the (1R,2S)-ephedrine salt of (S)-6-fluoro-4-ureidochroman-4-carboxylic acid and 68 ml of glacial acetic acid was heated at 95° C. for 1 hour, and then it was evaporated in vacuo at 60° C. This afforded 20 g of an oily residue which was diluted with 50 ml of water at 60° C. and then 50 ml of water at 10° C. The resulting slurry was adjusted to pH 4.5 with 4N sodium hydroxide and the solid was recovered by filtration to give 4.7 g of crude title product, mp 234°–240° C., [alpha]$_D^{25}$ = +50.5° (c=1, methanol). This crude product (4.0 g) was dissolved in 60 ml of boiling absolute ethanol, and the ethanol solution was filtered and cooled to 24° C. The solid was recovered by filtration, to give 2.0 g of (S)(+)-6-fluoro-spiro-[chroman-4,4′-imidazolidine]-2′,5′-dione, mp 240.5–243.0, [alpha]$_D^{25}$ = +55.4° (c=1, methanol).

I claim:

1. A process for the regeneration of 6-fluoro-4-chromanone from (R)-6-fluoro-4-ureidochroman-4-carboxylic acid or a mixture of (R)- and (RS)-6-fluoro-4-ureidochroman-4-carboxylic acid, which comprises:
    reacting said (R)-6-fluoro-4-ureidochroman-4-carboxylic acid or mixture of (R)- and (RS)-6-fluoro-4-ureidochroman-4-carboxylic acid with a metal permanganate, in an aqueous or partially aqueous solvent system, at a temperature in the range from 10° to 70° C., and at a pH in the range from 3.0 to 7.0.

2. The process according to claim 1, wherein said metal permanganate is an alkali metal permanganate.

3. The process according to claim 2, wherein said alkali metal permanganate is potassium permanganate.

4. The process according to claim 3, wherein the solvent system is substantially aqueous.

5. The process according to claim 4, wherein 0.7 to 2.0 molar equivalents of potassium permanganate is used.

6. The process according to claim 5, wherein 1.0 to 1.2 molar equivalents of potassium permanganate is used.

7. The process according to claim 5, wherein the pH of 3.0 to 7.0 is achieved by the addition of an acid selected from the group consisting of hydrochloric acid, sulfuric acid, nitric acid, phosphoric acid, acetic acid, methanesulfonic acid, benzenesulfonic acid and toluenesulfonic acids.

8. The process according to claim 7, wherein said acid is acetic acid.

9. The process according to claim 8, wherein the 6-fluoro-4-chromanone is regenerated from a mixture of (R)- and (RS)-6-fluoro-4-ureidochroman-4-carboxylic acid.

10. The process according to claim 9, wherein the ratio of said (R)- to said (RS)-6-fluoro-4-ureidochroman-4-carboxylic acid is in the range from 20:1 to 1:2.

11. The process according to claim 10, wherein said solvent system is water containing from 0.5 to 3 percent of glacial acetic acid by volume.

* * * * *

UNITED STATES PATENT AND TRADEMARK OFFICE
CERTIFICATE OF CORRECTION

PATENT NO. : 4,551,542
DATED : NOVEMBER 5, 1985
INVENTOR(S) : BERNARD S. MOORE

It is certified that error appears in the above-identified patent and that said Letters Patent is hereby corrected as shown below:

Column 1, lines 27 to 35, that portion of the formula reading

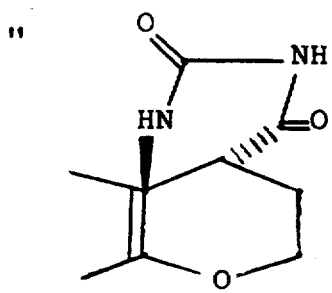   should read   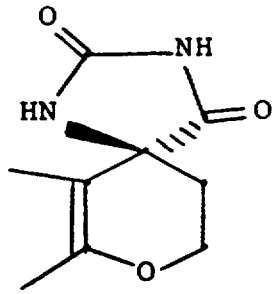

Signed and Sealed this

Eighteenth Day of February 1986

[SEAL]

Attest:

DONALD J. QUIGG

Attesting Officer

Commissioner of Patents and Trademarks